US011357433B2

(12) United States Patent
Lawrence et al.

(10) Patent No.: US 11,357,433 B2
(45) Date of Patent: *Jun. 14, 2022

(54) METHODS AND APPARATUS TO GATHER AND ANALYZE ELECTROENCEPHALOGRAPHIC DATA

(71) Applicant: The Nielsen Company (US), LLC, New York, NY (US)

(72) Inventors: Bradley R. Lawrence, Tampa, FL (US); Michael A. Hicks, Clearwater, FL (US)

(73) Assignee: Nielsen Consumer LLC, New York, NY (US)

( * ) Notice: Subject to any disclaimer, the term of this patent is extended or adjusted under 35 U.S.C. 154(b) by 1207 days.

This patent is subject to a terminal disclaimer.

(21) Appl. No.: 15/192,659

(22) Filed: Jun. 24, 2016

(65) Prior Publication Data

US 2016/0302683 A1    Oct. 20, 2016

Related U.S. Application Data

(63) Continuation of application No. 14/206,529, filed on Mar. 12, 2014, now Pat. No. 9,398,864.

(51) Int. Cl.
*A61B 5/00* (2006.01)
*A61B 5/291* (2021.01)
*A61B 5/16* (2006.01)

(52) U.S. Cl.
CPC .............. *A61B 5/291* (2021.01); *A61B 5/165* (2013.01); *A61B 5/6803* (2013.01);
(Continued)

(58) Field of Classification Search
CPC ..... A61B 5/0478; A61B 5/165; A61B 5/6803; A61B 5/6814; A61B 5/7221;
(Continued)

(56) References Cited

U.S. PATENT DOCUMENTS 2,409,033 A    10/1946   Garceau
3,508,541 A     4/1970   Westbrook et al.
(Continued)

FOREIGN PATENT DOCUMENTS

CN    1708328       12/2005
CN    102448371      5/2012
(Continued)

OTHER PUBLICATIONS

Mexican Industrial Property Institute, "Office Action," issued in connection with Mexican Patent Application No. MX/a/2016/009407, dated Dec. 3, 2018, 7 pages.
(Continued)

*Primary Examiner* — Eun Hwa Kim
*Assistant Examiner* — Adam Z Minchella
(74) *Attorney, Agent, or Firm* — Hanley, Flight & Zimmerman, LLC

(57) ABSTRACT

Example headsets and methods for gathering electroencephalographic signals are disclosed herein. An example headset disclosed herein includes a cap to be worn on a head of a person and a first electrode carried by the cap. The first electrode holder defines a first opening therethrough. The example headset includes a first electrode that insertable into the first opening. The first electrode has a first length and is adjustable in the first opening to a first plurality of discrete positions having different depths of insertion relative to the first opening. The first electrode is to engage the head of the person when inserted a sufficient depth into the first opening. The example headset also includes a second electrode that is interchangeable with the first electrode and insertable into the first opening. The second electrode has a second length, greater than the first length, and is adjustable in the first opening to a second plurality of discrete positions having different depths of insertion relative to the first opening. The
(Continued)

second electrode is to engage the head of the person when inserted a sufficient depth into the first opening.

20 Claims, 8 Drawing Sheets

(52) U.S. Cl.
CPC .......... *A61B 5/6814* (2013.01); *A61B 5/7221* (2013.01); *A61B 5/6844* (2013.01)

(58) Field of Classification Search
CPC ......... A61B 5/6844; A61B 5/291; A61B 5/25; A61B 5/256; A61B 5/257; A61B 5/259; A61B 5/271; A61B 5/273; A61B 5/274; A61N 1/0484; A61N 1/0424; A61N 1/04; A61N 1/02
See application file for complete search history.

(56) References Cited

U.S. PATENT DOCUMENTS

| | | | |
|---|---|---|---|
| 4,268,101 A * | 5/1981 | Stone | A61B 5/274 439/86 |
| 4,683,892 A | 8/1987 | Johansson | |
| 4,709,702 A | 12/1987 | Sherwin | |
| 4,967,038 A | 10/1990 | Gevins et al. | |
| 6,128,521 A | 10/2000 | Marro et al. | |
| 6,201,982 B1 | 3/2001 | Menkes et al. | |
| 6,574,513 B1 | 6/2003 | Collura et al. | |
| 6,708,051 B1 | 3/2004 | Durousseau | |
| 7,302,298 B2 | 11/2007 | Lowry et al. | |
| 8,548,554 B2 | 10/2013 | Popescu et al. | |
| 8,718,777 B2 | 5/2014 | Lowry et al. | |
| 9,398,864 B2 * | 7/2016 | Lawrence | A61B 5/7221 |
| 2002/0029005 A1 * | 3/2002 | Levendowski | A61B 5/291 600/545 |
| 2004/0102828 A1 | 5/2004 | Lowry et al. | |
| 2005/0075680 A1 | 4/2005 | Lowry et al. | |
| 2007/0093706 A1 * | 4/2007 | Gevins | A61B 5/291 600/383 |
| 2007/0225585 A1 | 9/2007 | Washbon et al. | |
| 2007/0238945 A1 | 10/2007 | Delic et al. | |
| 2007/0255127 A1 * | 11/2007 | Mintz | A61B 5/0476 600/383 |
| 2008/0027345 A1 * | 1/2008 | Kumada | A61B 5/0478 600/383 |
| 2008/0071323 A1 | 3/2008 | Lowry et al. | |
| 2008/0275359 A1 | 11/2008 | Mintz et al. | |
| 2009/0030298 A1 * | 1/2009 | Matthews | A61B 5/04 600/383 |
| 2009/0105576 A1 * | 4/2009 | Do | A61B 5/0478 600/382 |
| 2009/0112077 A1 | 4/2009 | Nguyen et al. | |
| 2009/0259137 A1 | 10/2009 | Delic et al. | |
| 2009/0292344 A1 | 11/2009 | Lowry et al. | |
| 2010/0198042 A1 | 8/2010 | Popescu et al. | |
| 2011/0054288 A1 * | 3/2011 | Besio | A61B 5/0478 600/383 |
| 2011/0237923 A1 * | 9/2011 | Picht | A61B 5/6843 600/383 |
| 2012/0143020 A1 * | 6/2012 | Bordoley | A61B 5/721 600/301 |
| 2012/0179062 A1 * | 7/2012 | Wilson | A61B 5/6839 600/544 |
| 2013/0274583 A1 * | 10/2013 | Heck | A61B 5/0488 600/383 |
| 2014/0012123 A1 | 1/2014 | Guger et al. | |

FOREIGN PATENT DOCUMENTS

| | | |
|---|---|---|
| CN | 102551700 | 7/2012 |
| CN | 106163393 | 11/2016 |
| FR | 2627975 | 9/1989 |
| JP | H0385005 | 8/1991 |
| JP | H10137261 | 5/1998 |
| JP | 2006000162 | 1/2006 |
| JP | 2006006667 | 1/2006 |
| JP | 2009514629 | 4/2009 |
| JP | 2009530064 | 8/2009 |
| JP | 2011120866 | 6/2011 |
| JP | 2012161419 | 8/2012 |
| JP | 2017510338 | 4/2017 |
| WO | 2012036639 | 3/2012 |
| WO | 2012150528 | 11/2012 |
| WO | 2013080992 | 6/2013 |
| WO | 2015138459 | 9/2015 |

OTHER PUBLICATIONS

Israel Patent Office, "Office Action", issued in connection with Israel Application No. 247734 dated Dec. 10, 2019, 5 pages.
China National Intellectual Property Administration, "Second Office Action", issued in connection with Chinese Application No. 201580013245.0 dated May 10, 2019, 23 pages.
Japanese Patent Office, "Notice of Reasons for Rejection", issued in connection with Japanese Patent Application No. 2017-199248 dated May 14, 2019, 6 pages.
Chinese National Intellectual Property Administration, "Office Action," English language version, Issued in connection with Chinese Patent Application No. 2015800132450, dated Sep. 3, 2018, 14 pages.
Japanese Patent Office, "Notice of Reasons for Rejection", English language version, issued in connection with Japanese Patent Application No. 2017199248, dated Sep. 11, 2018, 4 pages.
Japanese Patent Office, "Notice of Reasons for Rejection," issued in connection with Japanese Patent Application No. 2016-554396, dated Jul. 18, 2017, 5 pages.
European Patent Office, "Extended European Search Report," issued in connection with European Patent Application No. 15761746.5, dated Oct. 9, 2017, 7 pages.
Mexican Patent Office, "Office Action," issued in connection with Mexican Patent Application No. MX/a/2016/009407, dated May 2, 2018, 3 pages.
Israel Patent Office, "Office Action," issued in connection with Israel Patent Application No. 247734, dated Jun. 17, 2018, 4 pages.
International Searching Authority, "International Search Report and Written Opinion," issued in connection with PCT Application No. PCT/US2015/019721, dated Jun. 16, 2015, 9 pages.
United States Patent and Trademark Office, "Notice of Allowance and Fee(s) Due," issued in connection with U.S. Appl. No. 14/206,529, dated Mar. 23, 2016, 22 pages.
United States Patent and Trademark Office, "Non-Final Office Action" issued in connection with U.S. Appl. No. 14/206,529, dated Dec. 24, 2015, 30 pages.
United States Patent and Trademark Office, "Restriction and/or Election Requirement," issued in connection with U.S. Appl. No. 14/206,529, dated Sep. 23, 2015, 7 pages.
Mexican Industrial Property Institute, "Office Action," issued in connection with Mexican Patent Application No. MX/a/2016/009407, dated Aug. 15, 2016, 2 pages.
International Searching Authority, "International Preliminary Report on Patentability," issued in connection with PCT Application No. PCT/US2015/019721, dated Sep. 22, 2016, 6 pages.
European Patent Office, "Examination Report", issued in connection with application No. 15761746.5 dated Jun. 15, 2020, 4 pages.
The Intellectual Property Office of the United Kingdom, "Examination Report", issued in connection with application No. GB1614625.0 dated Jul. 30, 2020, 3 pages.
Intellectual Property India, "Examination Report", issued in connection with Application No. 201617023931, dated Oct. 21, 2020, 6 pages.
Intellectual Property Office, "Examination Report," issued in connection with Application No. GB1614625.0, dated Nov. 26, 2020, 4 pages.

(56) References Cited

OTHER PUBLICATIONS

Japanese Patent Office, "Notice of Reasons for Rejection," issued in connection with Patent Application No. 2020-017327, dated Feb. 9, 2021, 6 pages.
State of Israel Ministry of Justice, "Notice of Deficiencies," issued in connection with Israel Patent Application No. 274733, dated Feb. 15, 2021, 4 pages.
UK Intellectual Property Office, "Notification of Grant," issued in connection with Patent Application No. GB1614625.0, dated Mar. 16, 2021, 2 pages.
Uk Intellectual Property Office, "Search and Examination Report," issued in connection with Patent Application No. GB2101444.4, dated Feb. 23, 2021, 6 pages.
European Patent Office, "Summons to Attend Oral Proceedings Pursuant to Rule 115(1) EPC," issued in connection with European Appl. No. 15761746.5, dated Nov. 9, 2021, 6 pages.

\* cited by examiner

US 11,357,433 B2

METHODS AND APPARATUS TO GATHER AND ANALYZE ELECTROENCEPHALOGRAPHIC DATA

RELATED APPLICATION

This patent arises from a continuation of U.S. application Ser. No. 14/206,529, titled "Methods and Apparatus to Gather and Analyze Electroencephalographic Data," and filed Mar. 12, 2014, which is hereby incorporated by reference in its entirety.

FIELD OF THE DISCLOSURE

This disclosure relates generally to neurological and physiological monitoring, and, more particularly, to methods and apparatus to gather and analyze electroencephalographic data.

BACKGROUND

Electroencephalography (EEG) involves measuring and recording electrical activity resulting from many neural processes associated with different portions of the brain. EEG data is typically measured using a plurality of electrodes disposed on or near the scalp of a person to measure voltage fluctuations resulting from this electrical activity within the neurons of the brain. In some instances, the electrodes are coupled directly to the scalp of the person. Alternatively, in other instances, the electrodes are incorporated into a headset that may be worn on the head of the person and which locates the electrodes along the scalp of the person.

DETAILED DESCRIPTION

Figure 1A:
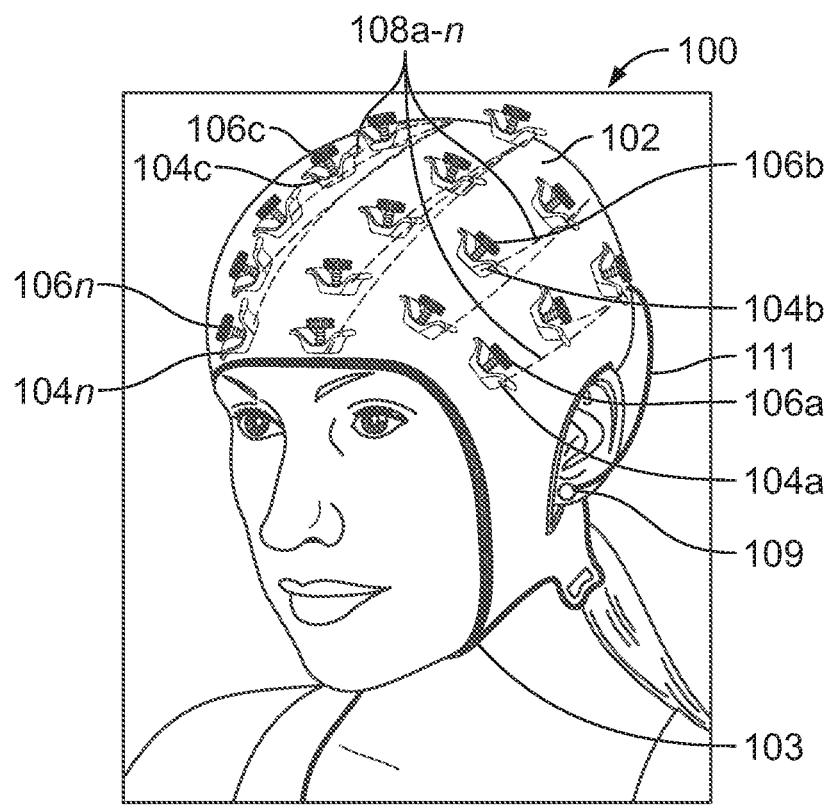
FIG. 1A is a perspective view of an example headset constructed in accordance with the teachings of this disclosure and including example electrode holders and example electrodes for gathering EEG signals.

Certain examples are shown in the above-identified figures and/or described in detail below. In describing these examples, like or identical reference numbers are used to identify the same or similar elements. Also, as used herein, two structures are "operatively coupled" when they are coupled directly or coupled indirectly (e.g., through one or more intervening structures and/or layers).

Electroencephalography (EEG) data is indicative of electrical activity of neurons (e.g., neural depolarization) in the brain. The neural electrical activity may be due to stimuli of one or more of the five senses (evoked activity) and/or from thought processes (spontaneous activity). Summations of these electrical activities (e.g., brainwaves) propagate to the surface (e.g., the scalp) and are detectable with electrodes. EEG data can be classified in multiple different frequency bands. Human brainwave frequencies include delta (approximately less than about 4 Hertz (Hz)), theta (approximately between about 3.5 Hz to about 7.5 Hz), alpha (approximately between about 7.5 Hz and about 13 Hz), beta (approximately between about 14 Hz and about 30 Hz) and gamma (approximately between about 30 Hz and about 100 Hz) frequency ranges. Skull and dermal layers tend to attenuate waves, particularly those above about 75 Hz.

EEG signals may be measured using one or more electrodes placed on a scalp of a person (e.g., a user, a viewer, a subject, a panelist, a participant or a patient) to measure voltage fluctuations resulting from electrical activity associated with post synaptic currents occurring within neurons of the person's brain. To enable surface EEG electrodes to receive signals effectively from the brain, the electrodes are placed close to the scalp. The electrodes may be manually placed upon a subject's head or may be contained in a wearable apparatus such as, for example, a headset. Some known EEG headsets utilize electrodes that are permanently fixed to the headset. A wire or cord is connected to the electrodes that transfers the signals gathered by the electrodes to a nearby computer or processing station. Thus, in such headsets, when an electrode is broken or otherwise inoperable, the entire headset may need to be replaced or significant maintenance is required to replace the inoperable electrode.

Additionally, to decrease impedance and improve signal quality, known headsets are typically strapped tightly onto a user's head to decrease the distance between the electrodes and the tissue of the scalp. However, too much pressure (e.g., greater than two Newtons per millimeter square ($N/mm^2$)) results in discomfort (e.g., pain) for most subjects. Also, in some instances, a user's hair is too long and/or thick to enable the known headset to operate well because the electrodes may not protrude all the way through the user's hair to contact the scalp.

Other known EEG headsets utilize a cap with holes for inserting wet EEG electrodes. With wet EEG electrodes, an operator applies a conductive gel into a hole of the cap and plugs an EEG electrode into the corresponding hole. The electrode is attached to a wire or cord that is also connected to the nearby computer or processing station. However, these gels are messy, and application of the gel is time consuming and requires consumables that need to be replenished. Additionally, in such an arrangement, specific electrodes are to be inserted into a particular corresponding hole so that the signals gathered by the electrode can be properly designated as associated with a particular area of the brain. Therefore, placing the wet EEG electrodes in the cap is time consuming, requires trained personnel, and is, thus, expensive.

Example headset(s) for receiving neuro-response data from a person's brain are disclosed herein. Example headsets disclosed herein comprise a plurality of example electrode holders disposed on a cap that is to be worn on the head of a person. In some examples, the electrode holders are disposed in specific locations on the cap for effective (e.g., optimum) reading. The specific locations may be, for example, over a particular part of the brain that emits certain brain waves of interest. In some examples, electrodes are inserted into the electrode holders to engage the scalp of the user and receive EEG signals. Example electrode holders disclosed herein are fixedly attached to the cap and are communicatively coupled to a wire or cord within the cap. In some examples, the wires or cords lead to a processor (e.g., a processor attached to the cap or a nearby computer or processing station) or a plug on the cap. In some such examples, the example electrodes are not permanently attached to a wire or cord. Instead, the electrodes removably engage corresponding ones of the electrodes holders. In some examples, the electrodes may be placed in any of the electrode holders.

When inserted into the electrode holders, the electrodes engage the scalp of a wearer of the cap. The signals gathered by one of the electrodes are transferred through the electrode, to the electrode holder and, thus, to the corresponding wire or cord coupled to the respective electrode holder. Thus, example electrodes disclosed herein may be easily inserted, removed, interchanged and/or replaced, which greatly reduces the time spent setting up and/or using the headset. As a result, if a single electrode is malfunctioning or otherwise inoperable, a user may remove the electrode and replace it, without disposing the entire cap.

Example electrodes disclosed herein are structured to be removably secured in a corresponding one of the example electrode holders. In some such examples, the electrode extends from an end of an electrode housing that includes a plurality of ribs along an outer surface of the electrode housing. The electrode holder of some such examples includes a retainer that engages the ribs and secures the electrode housing in place. In some examples, the electrode housing is movable up and/or down in the electrode holder, via the ribs and retainer interaction, to position the electrode closer to or further from the scalp of the user. This adjustability allows the electrode to be moved relative to the scalp (e.g., sufficiently close to the scalp to collect a good signal without causing discomfort) thereby increasing both signal collection quality and wearability (e.g., comfort).

Some example electrode holders disclosed herein are capable of accommodating electrodes of multiple different sizes. For example, an electrode of a first length may be used with a user who has short hair and/or fine hair. A relatively longer electrode may be used with a user who has longer or thicker hair so that the electrode extends all the way through the user's hair to engage the user's scalp. As a result, example headsets disclosed herein are customizable to accommodate different persons having different head shapes, hair lengths and/or hair thicknesses.

In some examples, the electrode is implemented as a pogo pin assembly. In some such examples, a spring is disposed within the electrode housing to bias the electrode pin outwards from the end of the electrode housing to engage the scalp of the user. The tension from the spring adjusts to the force applied to the head and further reduces discomfort when the electrode pin engages the scalp. As a result, the spring increases wearability without compromising signal collection quality.

An example headset disclosed herein includes a cap to be worn on a head of a person and a first electrode holder carried by the cap. In some examples, the first electrode holder defines a first opening therethrough. The example headset of some such examples includes a first electrode that is insertable into the first opening. The first electrode of some such examples has a first length and is adjustable in the first opening to a first plurality of discrete positions having different depths of insertion relative to the first opening. In some such examples, the first electrode is to engage the head of the person when inserted a sufficient depth into the first opening. The example headset of some examples also includes a second electrode that is interchangeable with the first electrode and insertable into the same first opening as the first electrode (with the first electrode removed). The second electrode of some such examples has a second length greater than the first length and is adjustable in the first opening to a second plurality of discrete positions having different depths of insertion relative to the first opening. The second electrode of some examples engages the head of the person when inserted a sufficient depth into the first opening.

In some examples, the first electrode includes an electrode housing and a pin that is retractable into the electrode housing. In some such examples, the first electrode includes a spring disposed within the electrode housing to bias the pin outwards. In some examples, the electrode housing includes a sheath having a plurality of ribs protruding from an outer surface of the sheath. In some examples, the first electrode holder includes a retainer disposed within the first opening. In some such examples, at least a portion of the plurality of ribs are to engage the retainer when the first electrode is disposed in the first opening to secure the first electrode at one of the different depths. In some examples, the plurality of ribs includes a first rib disposed a first distance from a first end of the sheath and a second rib disposed a second distance from the first end of the sheath. In some examples, the second distance is greater than the first distance. In some such examples, the force of the first electrode against the head of the person when wearing the cap is greater when the second rib is engaged with the retainer than when the first rib is engaged with the retainer.

In some examples, the ribs are adjustably coupled to the first electrode holder when the first electrode is disposed in the first opening. In some examples, the ribs are adjustable by screwing the ribs into the respective electrode holder. In other examples, the ribs are not helical and adjustably coupled to the first electrode holder via a non-screwing motion. In some examples, the non-screwing motion includes a sliding motion, a friction fit, etc. In some examples, the non-screwing motion includes a snap fit.

In some examples, the ribs and the first electrode holder are rotatably coupled when the first electrode is disposed in the first opening. In some examples, the first opening defines a first passage through the cap. In some examples, the retainer is communicatively coupled to a wire disposed within the cap.

In some examples, the electrode housing includes a handle. In some examples, the handle comprises a first material and the sheath and the pin comprise of a second material, which is different than the first material. In some such examples, the first material is an insulator.

In some examples, the first electrode holder includes a grip extending away from the first electrode when the first electrode is in the first electrode holder.

Some example headsets include a second electrode holder carried by the cap. In some examples, the second electrode holder has a second opening therethrough. Some examples include a third electrode insertable into the second passage. In some examples, the first electrode is interchangeable with the third electrode and insertable into the second opening.

Example methods disclosed herein include placing a cap on a head of a person, the cap having a first electrode holder comprising a base, an opening extending through the base and a retainer operatively coupled to the base within the opening. Some example methods include inserting an electrode into the opening of the base while the cap is disposed on the head of the person. In some example methods, the electrode includes an elongated sheath having a plurality of ribs to engage the retainer. Some example methods also include adjusting a depth of the electrode within the opening by removably securing the electrode in one of a plurality of discrete positions having different depths of insertion relative to the opening defined by an interface between the plurality of ribs and the retainer.

Some example methods include indicating when the electrode is inserted in the opening and engaged with the retainer. Some example methods further include indicating when the electrode is in contact with the head of the person.

Some example methods include analyzing a quality of a signal gathered by the electrode, performing a comparison of the quality to a threshold quality, determining that the quality is acceptable or unacceptable based on the comparison and indicating whether the quality is unacceptable. Some example methods include adjusting the cap on the head of the person.

Figure 1B:
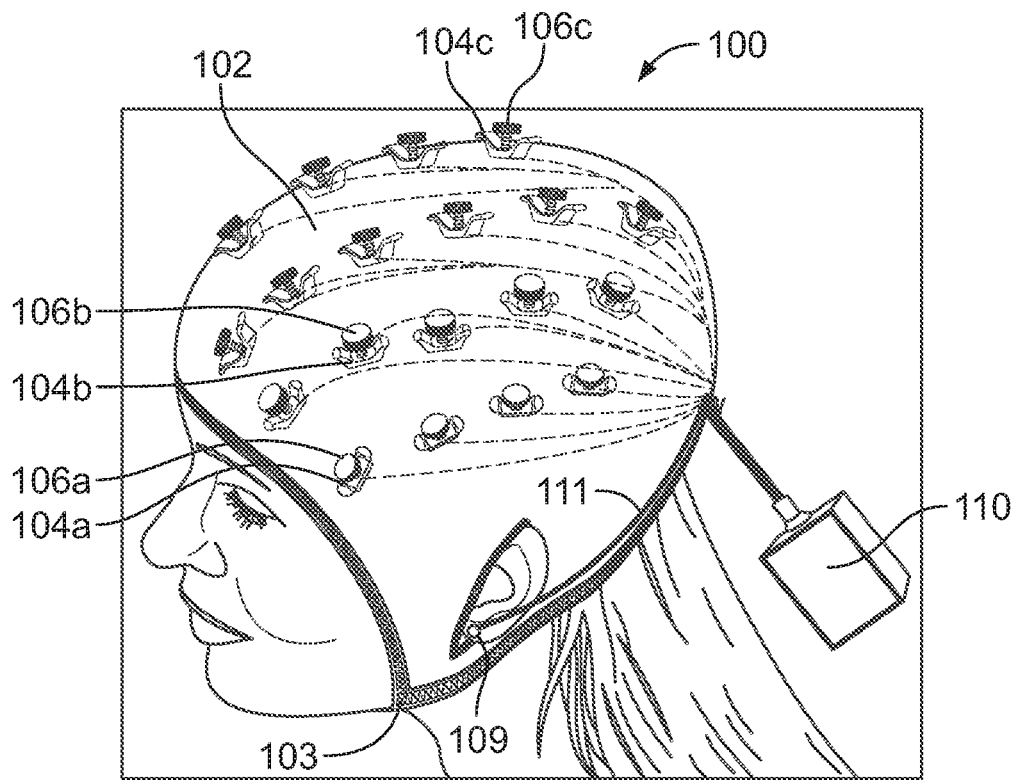
FIG. 1B is a left side view of the example headset shown in FIG. 1A.

Turning now to the figures, FIGS. 1A and 1B show an example headset 100 constructed in accordance with the teachings of this disclosure for gathering EEG signals from the head of a person. The example headset 100 of FIGS. 1A and 1B may be used, for instance, to gather medical information from a patient in a medical or a home environment, to control aspects of a game or other entertainment device, to provide data as part of a fitness regime, to collect audience measurement data, to control remote devices and/or for multiple other uses. The example headset 100 of FIGS. 1A and 1B is intended to be worn on the head of a person, a user, a subject, a viewer, a participant and/or panelist.

The example headset 100 of FIGS. 1A and 1B includes a cap 102 (e.g., a base, a cover, headgear) that is to be disposed (e.g., worn) on the head of a person. In the illustrated example, the cap 102 is comprised of a flexible and/or stretchable material such as, for example, nylon, plastic, rubber, etc. In some examples, the cap 102 includes a chin strap 103 for tightening the cap 102 against the head of the user. In other examples, alternative and/or additional buckles and/or straps are employed to tighten and/or secure the cap 102 on the head of the person.

As shown in the illustrated example of FIGS. 1A and 1B, the headset 100 includes a plurality of electrode holders 104a-n operatively coupled to the cap 102. The electrode holders 104a-n of the illustrated example are adapted to receive electrodes 106a-n for gathering EEG signals from the scalp of a user. More specifically, each of the electrode holders 104a-n removably secures a respective electrode 106a-n to the cap 102. The electrode holders 104a-n are disposed in fixed locations on the cap 102 to locate the electrodes 106a-n at or near desired areas (e.g., near a particular area of the brain that emits a certain signal for a certain response) for good (e.g., near optimum) electrode contact and/or data collection. In the illustrated example there are multiple electrode sites. In some examples, the electrode holders 104a-n are placed in specific locations to comply with the International 10-20 system, which is a standard of electrode placement on the scalp to ensure standardized reproducibility. These sites provide coverage of all the lobes of the brain including frontal, parietal, occipital and temporal. Additionally, these sites are the accepted EEG electrode sites for a clinically valid EEG. In other examples, the headset 100 may include more or fewer electrode holders and/or electrodes.

The cap 102 of the illustrated example includes a plurality of wires 108a-n disposed on, under, and/or within the cap 102 (e.g., under the cap, on top of the cap, within the material of the cap or between two layers of material comprising the cap). The wires 108a-n of the illustrated example are communicatively coupled (e.g., in circuit with, in electrical contact with, etc.) to the electrode holders 104a-n, respectively. In the illustrated example, the wires 108a-n run through the cap and connect to a processing unit 110 (FIG. 1B) disposed in the rear of cap 102. The wires 108a-n of the illustrated example carry the signals gathered by the electrodes 106a-n to the processing unit 110. In some examples, traces, communication links, a ribbon, a flexible printed circuit board (FPCB), and/or other suitable communication links may be used in addition to or alternatively to the wires 108a-n. In other examples, the electrode holders 106a-n are wirelessly coupled to the processing unit 110 and/or to a remote processor. For example, one or more of the electrode holders 104a-n may include a transmitter to wirelessly transmit signals (e.g., EEG signals) to the processing unit 110.

In the illustrated example, the wires 108a-n are disposed between a top layer of material and a bottom layer of material in the cap 102. In such an example, the top layer of material comprises a conductive material (e.g., a conductive mesh) that provides a Faraday cage to prevent external static and non-static electric fields from interfering with the EEG signals. By disposing the wires 108a-n within the material of the cap 102, the wires 108a-n are also less likely to be caught or snagged on objects.

In some examples, an electrode is employed to provide a reference signal for comparing with the EEG signals gathered from other parts of the person's head by, for example, the example headset 100 of FIGS. 1A and 1B. A reference electrode is positioned at a point on the person's body that has minimal or no EEG activity or other artifacts and/or noise such as, for example, those indicative of muscle contractions or blood flow. In the illustrated example of FIGS. 1A and 1B, the headset 100 includes a reference electrode 109 that may be attached to the ear (e.g., the earlobe) of the wearer. A wire 111 communicatively couples the electrode 109 to the processing unit 110. The reference electrode 109 of the illustrated example may be a wet electrode (e.g., a one use gel sensor) or a dry electrode (e.g., a flat metal pad) and may be attached to the ear of the wearer using any suitable fastening mechanism(s) such as, for example, an adhesive or a clip. An example of a clip for attaching an electrode to an earlobe of a person is disclosed in U.S. patent application Ser. No. 13/829,849 titled "METHODS AND APPARATUS TO GATHER AND ANALYZE ELECTROENCEPHALOGRAPHIC DATA," filed Mar. 14, 2013, which is incorporated herein by reference in its entirety.

In the example headset 100 of FIGS. 1A and 1B, a single reference electrode 109 is implemented and attached to the ear of the person wearing the headset 100. However, in other examples, the reference electrode 109 may be attached to the nose, the neck, or any other location on the person capable of providing a reference signal. Additionally, in some examples, more than one reference electrode is implemented.

In the illustrated example, the processing unit 110 houses electrical components for processing signals gathered from the electrodes 106a-n and the reference electrode 109 (described in further detail below). In some examples, the electrical components are used, for example, to convert the EEG data from analog data to digital data, amplify the EEG data, filter (e.g., remove noise from) the data, analyze the data and/or transmit the data to a computer or other remote receiver or processing unit. In some examples, the processing unit 110 includes hardware and software such as, for example, an amplifier, signal conditioning circuitry, a semiconductor based micro-processor and/or a transmitter for transmitting signals to a data center or a computer. In other examples, some of the processing occurs at the headset 100 and some processing occurs remotely after the headset 100 transmits data or semi-processed results to a remote site such as, for example, via a wireless connection. In some examples, the processing unit 110 is removably attached to the headset 100. In some such examples, the processing unit 110 may be removed and replaced with a different processing unit that may have, for example, different programming functions and analysis tools. In some examples, a plurality of processing units may contain different preprogrammed analysis tools and the processing units may be interchanged depending on the desired function (e.g., controlling a game, collecting medical information, controlling household appliances, etc.) of the headset 100.

In some examples, the headset 100 does not include the processing unit 110 and, instead, the wires 108a-n, 111 lead to a plug (e.g., a pin connector), which may be used to plug the headset directly to another computer or processing station. In still other examples, the processing unit 100 includes only an amplifier to amplify the EEG signals. In some such examples, the processing unit 100 may be plugged into another computer or processing station for further processing and/or may wireless transmit the amplified signals to the computer and/or processing station. In some examples, it is advantageous to amplify the signals as close to the electrodes as possible.

Figure 2A:
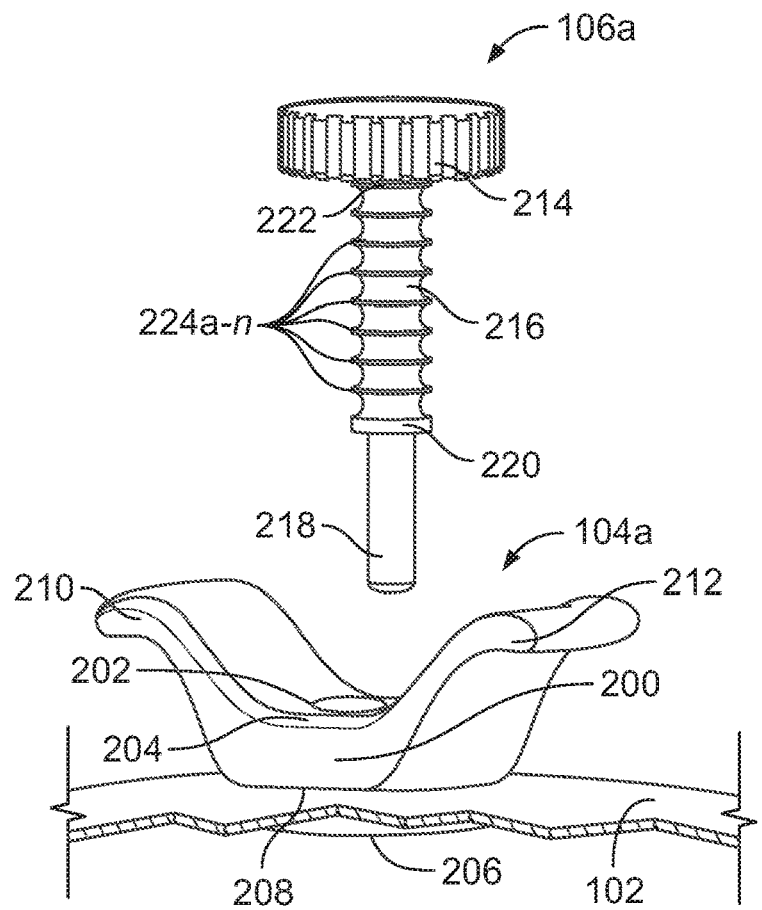
FIG. 2A is an exploded view of an example implementation of one of the example electrode holders and the example electrodes of FIGS. 1A and 1B.

FIG. 2A is an exploded view of an example implementation of one of the plurality of electrodes 106a and one of the plurality of electrode holders 104a of FIGS. 1A and 1B. In the illustrated example, the electrode holder 106a includes a support or base 200 defining a passage or opening 202 therethrough. In the illustrated example, the opening 202 extends through the base 200 from a top surface 204 of the base 200 to a bottom surface 206 of the base 200. The base 200 also has an annular groove 208 where the cap 102 is operatively coupled to the electrode holder 104a. The electrode holder 104a of the illustrated example further includes a first curved extension 210 and a second curved extension 212, which project upward from the base 200 and extend outward (e.g., away from the electrode 106a). In some examples, the first and second curved extensions 212 are grips that are used as finger tabs to allow a user to easily insert the electrode 106a into the electrode holder 104a, described in further detail below. Though curved extensions 210, 212 are shown in the illustrated example, other suitable shape(s) may additionally and/or alternatively be used.

Figure 2B:
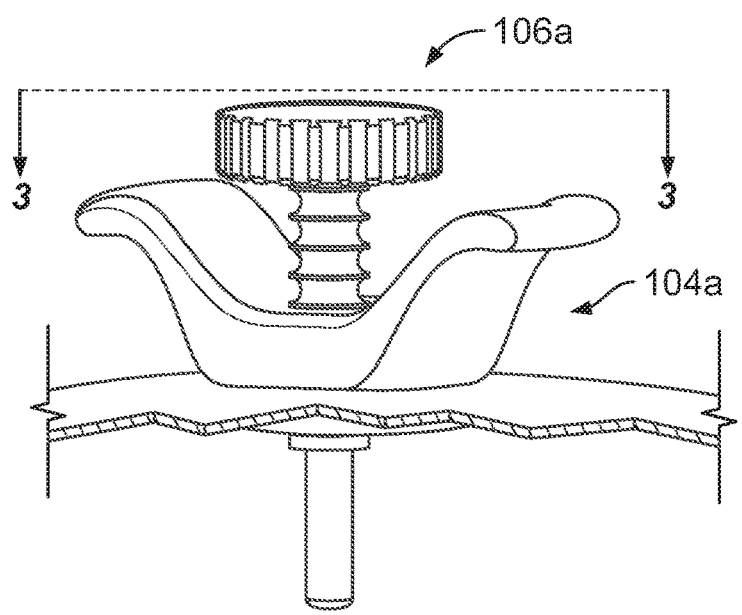
FIG. 2B is an assembled view of the example electrode holder and the example electrode of FIG. 2A.

As shown in FIG. 2A, the electrode 106a includes a handle 214 and an electrode body comprising a housing or sheath 216 and a pin 218 (e.g., a pogo pin). In the illustrated example, the sheath 216 receives the pin 218. The pin 218 of the illustrated example is retractable into the sheath 216 and biased outward from the sheath 216 by a spring (described in further detail below). Specifically, the pin 218 is retractable into a bottom end 220 of the sheath 216 and the handle 214 is coupled to a top end 222 of the sheath 216. As shown in FIGS. 2A and 2B, the sheath 216 of the illustrated example includes a plurality of ribs 224a-n (e.g., first engagement members). The ribs 224a-n are protrusions extending outward from the sheath 216. In the example shown, the sheath 216 has seven ribs. However, in other examples, the sheath 216 may have more or fewer ribs (e.g., two ribs, twenty ribs, etc.).

The electrode 106a of the illustrated example is insertable into the electrode holder 104a. Specifically, a user may position the electrode 106a above the opening 202 (e.g., the position shown in FIG. 2A) of the electrode holder 104a and insert the electrode 106a into the electrode holder 104a (e.g., the position shown in FIG. 2B) by applying a downward force (e.g., a force toward the scalp of the user wearing the cap). The ribs 224a-n of the sheath 216 engage a retainer ring (e.g., a second engagement member) (described below) inside the opening 202 of the base 200 to secure the electrode 106a in one of a plurality of discrete positions in the electrode holder 104a. The ribs 224a-n allow the electrode 106a to lock and/or snap into position once inserted into the opening 202. Each rib defines a different, discrete position or depth that the electrode 106a may be inserted into the opening 202 of the electrode holder 104a. Thus, the depth of the electrode 106a in the electrode holder 104a may be adjusted.

FIG. 2B shows the example electrode 106a of FIG. 2A inserted into the electrode holder 104a. In an example operation, a user can place a first finger (e.g., an index finger) under the first curved extension 210 and a second finger (e.g., a middle finger) under the second curved extension 212. In this manner, the user can use his/her thumb and/or palm to press on the top of the handle 214 to insert the electrode 106a into the electrode holder 104a. The user may push the electrode 106a into the electrode holder 104a and the electrode 106a releasably locks or snaps into engagement at the ribs 224a-n. The electrode 106a may be pressed downward until the pin 218 engages the scalp of the user and may be further adjusted (e.g., pulled in or out) depending on the desired pressure to be applied to the scalp. As the pin 218 engages the head of the user, the cap 102 is forced upward and away from the head and, thus, creates a downward tension in the cap 102. This downward tension or biasing force assists in keeping the pin 218 against the scalp of the user and the cap 102 secure and stabile on the user's head. In some examples, the cap 102 being forced upward (e.g., away from the head of the user) provides a visual indication that the electrode 106a is engaged with the head. In addition, the pin 218 of the illustrated example is retractable into the sheath 216 against the force of the spring (FIG. 3), which softens the force of the pin 218 against the scalp. This dual adjustability greatly increases the wearability of the cap 102 and enables a user to more effectively situate the electrode 106a against the scalp for good signal quality without discomfort for the wearer of the cap.

Figure 3:
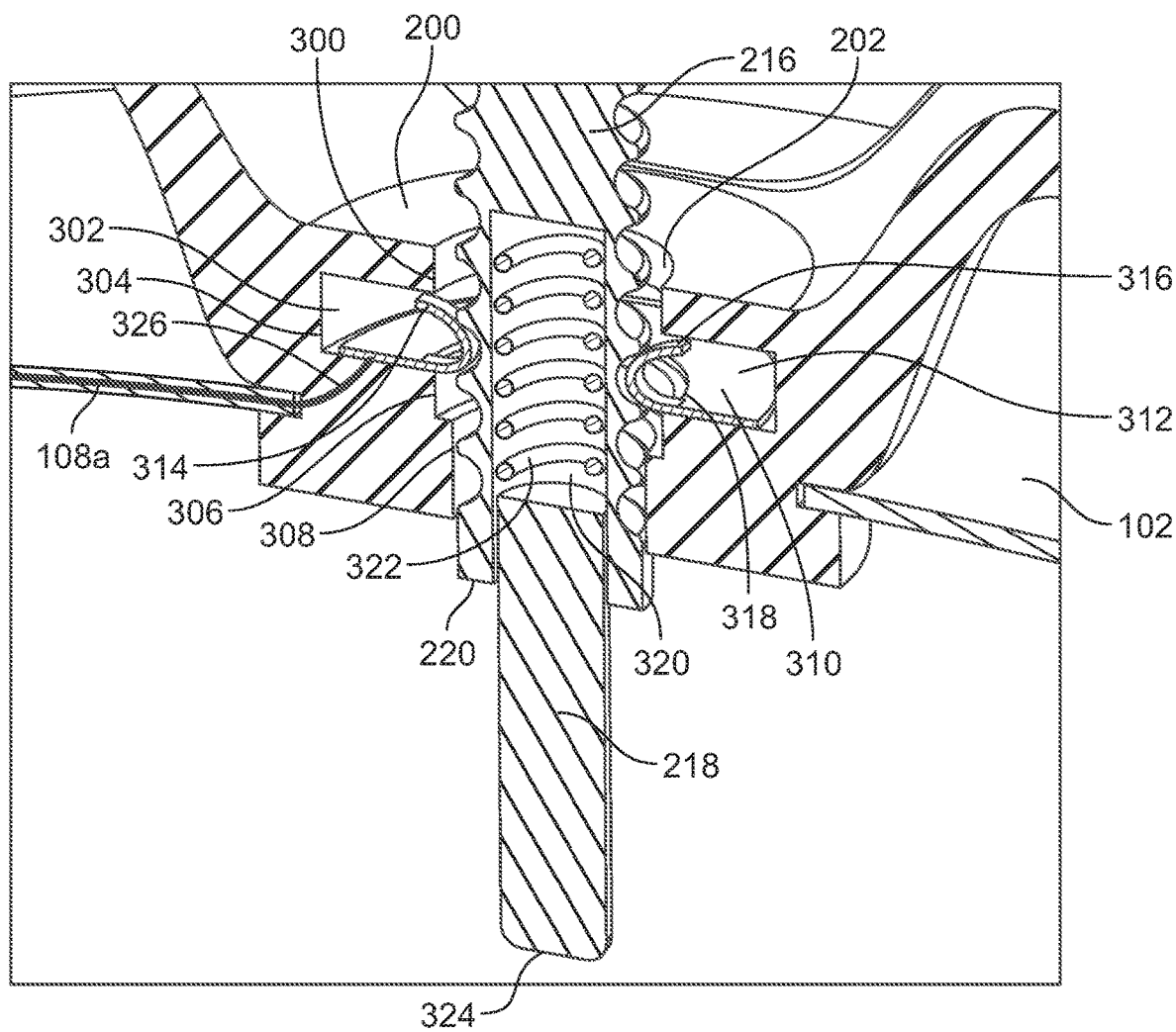
FIG. 3 is a cross-sectioned view of a portion of the example electrode holder and the example electrode of FIGS. 2A and 2B taken along line 3-3 of FIG. 2B.

FIG. 3 is a cross-sectional view of the example electrode 106a inserted into the example electrode holder 104a taken along line 3-3 of FIG. 2B. In the illustrated example, the opening 204 of the electrode holder 104a includes a first aperture 300 having a first diameter, an annular cavity 302 having a second diameter 304, a third aperture 306 having a third diameter and a fourth aperture 308 having a fourth diameter. The first, second, third and fourth apertures 300, 302, 306, 308 define the inside of the opening 204 (e.g., a passage through the base 200 and cap 102). In other examples, the electrode holder 104a may include more or less apertures to define the opening 204. In addition, in some examples, a single electrode holder 104a includes multiple openings that are parallel to each other to accommodate multiple electrodes.

As shown in the example of FIG. 3, a retainer ring 310 is disposed within the annular cavity 302 of the electrode holder 104a. The retainer ring 310 of the illustrated example includes a disk 312 and first and second springs 314, 316 that are operatively coupled to an inner edge 318 of the disk 312. In the illustrated example, the first and second springs 314, 316 are U-shaped springs. In other examples, there may be one spring. In some such examples, the lone spring may be formed of an annular ring that surrounds an inserted electrode.

As the electrode 106a of the illustrated example is inserted into the opening 202 of the electrode holder 104a, the ribs 224a-n engage and/or slide past the springs 314, 316 and force the springs 314, 316 to bend radially outwards. When one of the plurality of ribs 224a-n is slid past the springs 314, 316, the springs 314a-316 flex radially inward, due to their biasing force, and engage a section of the sheath 216 between two of the ribs 224a-n. In this position, the springs 314, 316 of the illustrated example secure and stabilize the electrode 106a and prevent the electrode 106a from moving up or down in the electrode holder 104a until a large enough force on the electrode 106a overcomes the force provided by the springs 314, 316. When such a force is applied, the electrode 106a is moved further into the base 206 or is removed from the base 206. During manufacturing, the tension of the springs 314, 316 can be selected to achieve a desired amount of force acting on the electrode 106a. For example, stiffer springs may be used to prevent the electrode 106a from moving in the electrode holder 104a when relatively smaller forces are acting on the electrode 106a.

In illustrated the example, the ribs 224a-n are individual annular rings formed around the sheath 216. The ribs 224a-n represent discrete positions that the electrode 106a may be held in the electrode holder 104. However, in other examples, the ribs 224a-n may be helical and form a thread (e.g., similar to a screw). In such an example, the electrode 106a may be screwed (e.g., rotated) into the electrode holder 104a. With a thread arrangement, the electrode 106a can be adjusted in continuous manner, with relatively greater refinement in the positioning. The thread arrangement also eliminates the need for the disk 312 to have spring properties.

In other examples, other types of engagement members may be used inside the opening 202 of the electrode holder 104a to secure the electrode 106a. In some examples, the inside of the opening 202 has a substantially flat wall from the top 204 of the base 200 to the bottom of the base 206 that has a protrusion or rib extending therefrom into the opening to engage the ribs 224a-n on the electrode 106a. In such an example, the protrusion may be electrically coupled to the wire 108a (e.g., via a wire or trace extending through the base 200).

In the illustrated example, the pin 218 of the electrode 106a engages the head of a user and receives EEG signals transmitted through the scalp. The pin 218 is retractable into a cavity 320 in the bottom end 220 of the sheath 216 and is biased outward via a spring 322, which is disposed within the cavity 320. A tip 324 of the pin 218 contacts the scalp of the head of a person and senses the EEG signals. The spring 322 allows the pin 218 to retract into the sheath 216 if too much force is applied downward against the scalp and, thus, increases the comfort and wearability of the headset 100. Different size springs may be utilized with the first electrode 212 to provide more or less force. In some examples, the spring 322 provides around two (2) Newtons of force. In addition, the distance at which the sheath 216 is inserted into the electrode holder 104a also affects the force applied against the scalp. For example, the force of the pin 218 against the scalp increases the further the sheath 216 is inserted into the electrode holder 104a. Also, in the illustrated example, the spring 322 is a coil spring. However, in other examples, the spring 322 may be implemented by any other type of spring such as, for example, a leaf spring.

In the illustrated example, the pin 218, the spring 322 and the sheath 216 are comprised of a conductive material such as, for example, silver, silver chloride, gold, platinum, titanium, etc. In some examples, the pin 218, the spring 322 and the sheath 216 are comprised of the same conductive material. However, in other examples, the pin 218, the spring 322 and/or the sheath 216 are comprised of different conductive materials. In the illustrated example, because the pin 218, the spring 322 and the sheath 216 are conductive, and in contact with each other, the signals gathered by the pin 218 are transferred through the pin 218, the spring 322 and the sheath 216. The signals are also transferred from the sheath 214 to the retainer ring 310 via electrical contact between the sheath 214 and the springs 314, 316 of the retainer ring 310. In the illustrated example, a wire 326 is disposed within the base 200 of the electrode holder 104a and communicatively couples (e.g., electrically couples) the retainer ring 310 and the wire 108a within the cap 102 at the annular groove 208. The wire 326 may be operatively coupled to the retainer using any suitable fastening mechanism such as, for example, welding, an adhesive, friction fit, etc. Thus, signals received by the pin 218 of the electrode 106a are transferred to the wiring of the cap 102 and, in some examples, to the processing unit 110 or other output cord or part elsewhere on the headset 100.

In the illustrated example, the handle 214 is comprised of an insulator. As a result, a person may touch the handle 214 of the electrode 106a without interfering with the EEG signals being transmitted through the sheath 218. In the illustrated example, the handle 214 is in the shape of a circular knob with grips. However, in other example, other suitable handles and/or shapes may be employed (e.g., a turnkey, a lever, etc.).

In an example operation, the cap 102 of the illustrated example is placed on the head of a person and the chin strap 103 is adjusted to change the tension of the cap 102 on the head. Once situated, an electrode (e.g., the electrode 106a) is inserted into an electrode holder (e.g., the electrode holder 104a). In some examples, the headset 100 is communicatively coupled to a computer or processing station for real-time processing and display. The computer or processing station may indicate when an electrode has been placed in a certain electrode holder. Then, the electrode may be pushed into the corresponding electrode holder until the pin of the electrode engages the scalp of the user with a desired level of pressure. In some examples, the computer or processing station may also indicate that the electrode has contacted the scalp of the user and signals are successfully being received by the electrode.

In the examples of FIGS. 2A, 2B and 3, the pin 218 and the sheath 216 are cylindrical and have circular cross-sections. However, in other examples, the pin 218 and/or the sheath 216 may have a rectangular, square or other shaped cross-section. In the illustrated example, the tip 324 of the first electrode pin 218 is flat, which provides a larger surface area to contact the scalp of the user than would a point. The larger surface area also increases the comfort level of the headset 100 by distributing the force over a larger area than would be the case in a pointed electrode. However, in other examples, the tip 324 of the pin 218 may be rounded or otherwise point shaped. The pin 218 of the electrode 106a is sized to protrude through the hair on a person's head, which provides sufficient surface area to contact the scalp of the user and receive signals from the brain. Different sized pins 218 may be used depending on the thickness of the hair.

Additionally, although a plurality of ribs 222a-n are shown in FIGS. 2A, 2B and 3 as covering a majority of the sheath 216, in other examples, the ribs 222a-n only cover a portion of the sheath. In such an example, the remainder of the sheath 216 may be smooth.

The other electrode holders 104b-n and electrodes 106b-n shown in the headset 100 in FIGS. 1A and 1B may be identical to the example electrode holder 104a and example electrode 106a shown in FIGS. 2A, 2B and 3. As a result, the electrodes 106a-n may be freely interchanged with other electrodes 106a-n. Thus, in the illustrated example, specific electrode holders 104a-n are not earmarked for only accepting a particular electrode 106a-n. Instead, any of the electrodes 106a-n may be inserted into any of the electrode holders 104a-n. As a result, if an electrode is malfunctioning, that malfunctioning electrode can be easily removed and replaced, without having to replace the entire headset 100.

While the example electrode holder 104a and the example electrode 106a are disclosed herein in relation to a stretchable or flexible cap 102, the example electrode 104a and the example electrode 106a are also capable of being incorporated into a rigid headset. Additionally or alternatively, the example electrode holder 104a and the example electrode 106a could be used in any other headset structure or base member capable of incorporating the electrode holder 104a. The interaction between the example electrode holder 104a and the example electrode 106a allow electrodes to be easily and quickly inserted, replaced, interchanged, etc. Additionally, because the wires 108a-n are in communication with (e.g., electrically connected to) the electrode holders 104a-n and the electrodes 106a-n may be used in any of the electrode holders 104a-n, the time spent setting up the headset is greatly reduced compared to prior headsets.

Figure 4:
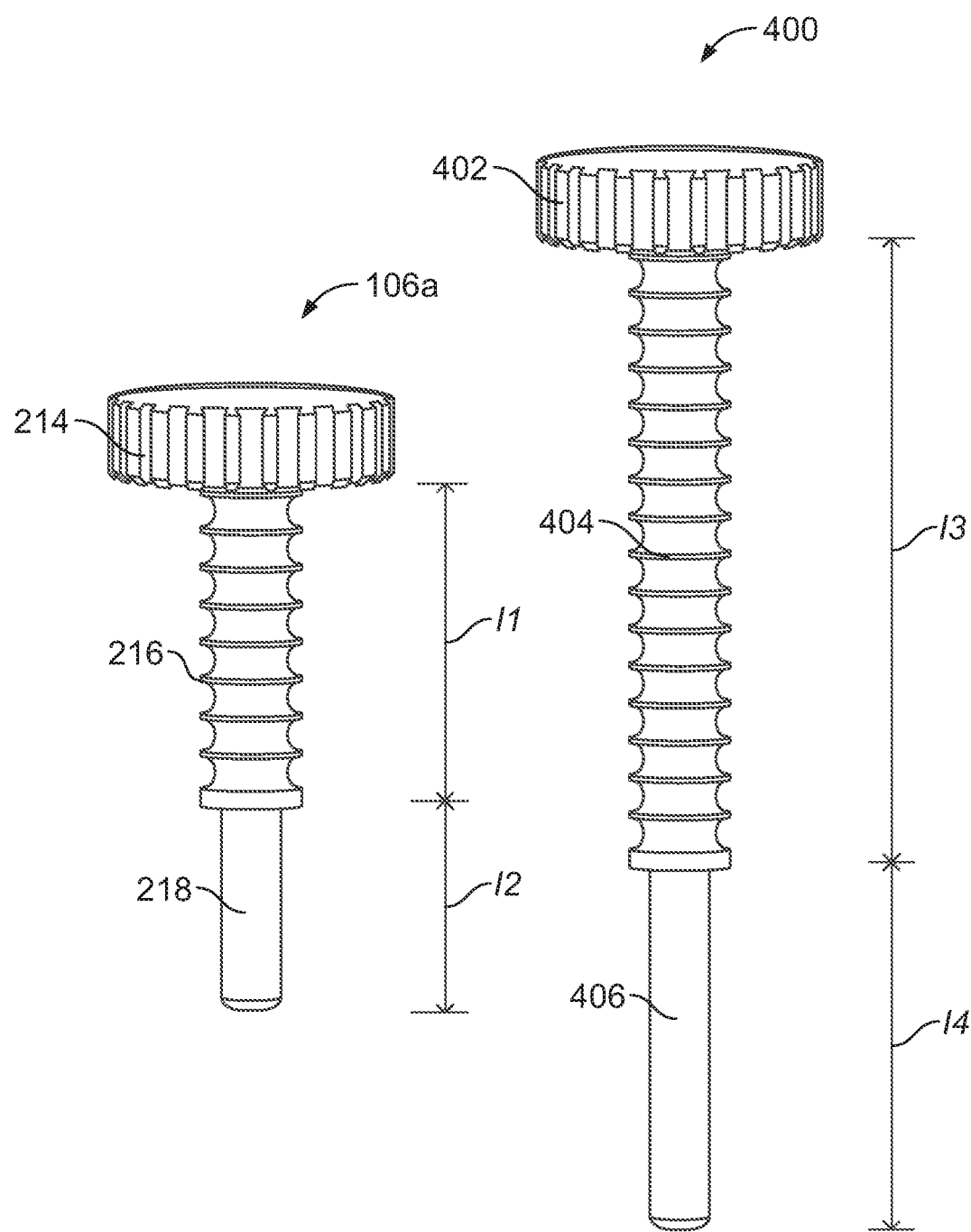
FIG. 4 illustrates different sized example electrodes that may be utilized with the example headset of FIGS. 1A and 1B.

FIG. 4 illustrates two different sized example electrodes that may be used with the example holders 104a-n disclosed herein. In some examples, when a user has longer and/or thicker hair, the electrode 106a may not be long enough to extend all the way through the hair to effectively engage the head of the user. In such an instance, the electrode 106a may be replaced with a longer electrode such as, for example, the electrode 400, which has a relatively longer sheath and pin compared to the electrode 106a. As mentioned above, the electrode 106a includes the handle 214, the sheath 216 and the pin 218. The sheath 216 of the electrode 106a has a length of l1, and the pin 218 of the electrode 106a has a length of l2. The electrode 400 is substantially similar to the electrode 106a and includes a handle 402, a sheath 404 and a pin 406 (which is retractable into the sheath 404). In the illustrated example, the sheath 404 of the electrode 400 has a length of l3, and the pin 406 of the electrode 400 has a length of l4. In some examples, l3 is about one to two inches. In the example shown, l3 is larger than l1, and l4 is larger than l2. In other examples, l4 is the same as l2 and l3 is larger than l1. Thus, the example electrodes disclosed herein may be manufactured in a range of sizes (e.g., lengths) to accommodate different hair thicknesses and/or head sizes. As mentioned above, a longer electrode such as the electrode 400 may be used when the user has thicker hair and a relatively shorter electrode (e.g., the electrode 106a) is not long enough to extend through the hair.

Figure 5:
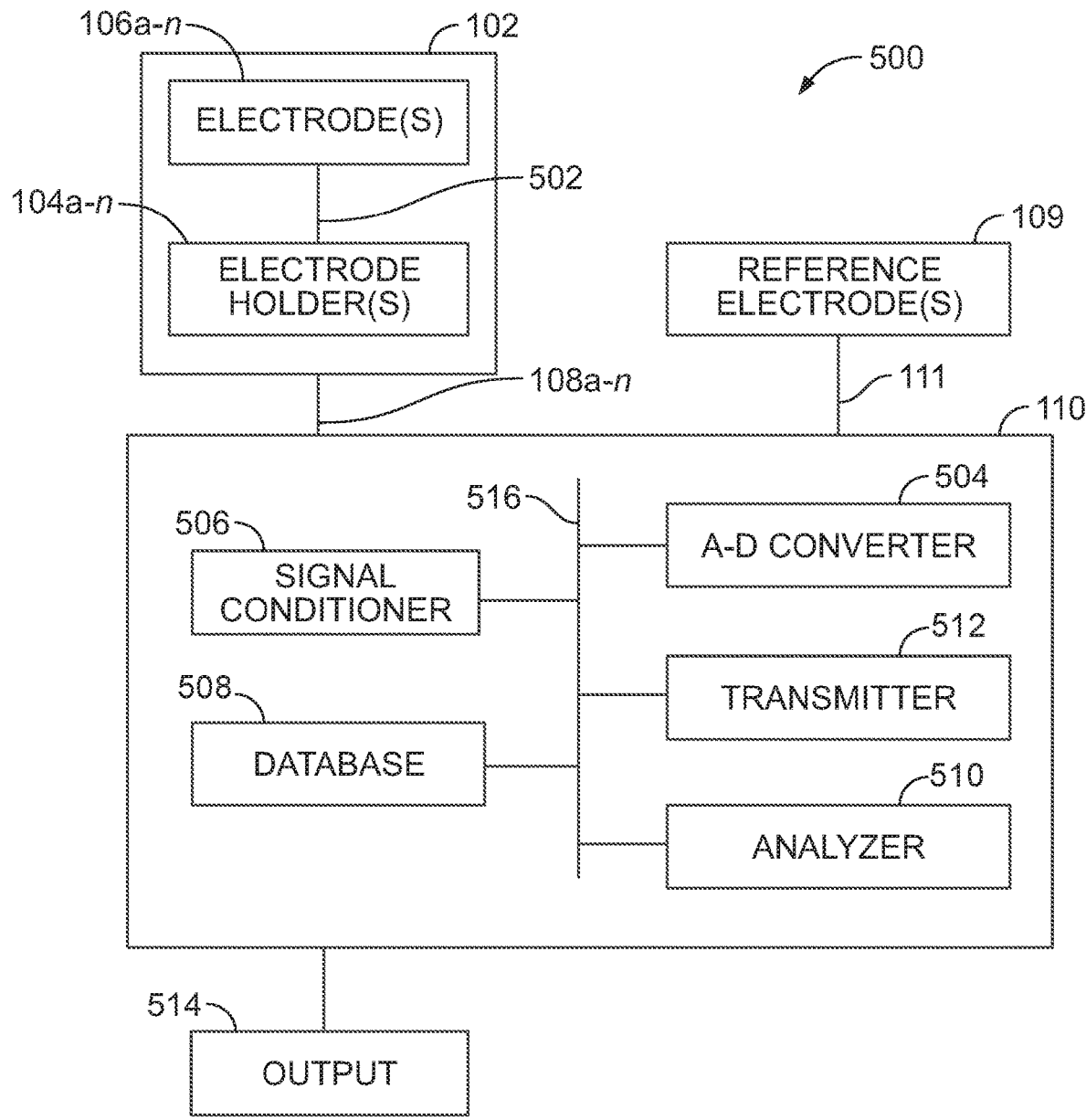
FIG. 5 is a block diagram of an example circuit from the example headset of FIGS. 1A and 1B.

FIG. 5 is a block diagram of an example processing system 500 for use with the example headset 100. The example system 500 of FIG. 5 includes a plurality of electrodes 106a-n. The electrodes 106a-n are coupled, for example, to a headset 100 to be worn on a head of a subject for gathering EEG data as explained above. The electrodes 106a-n are coupled to electrode holders 104a-n, which are coupled to a processor unit 110 of the headset 100 shown in FIGS. 1A-1B.

In the system 500 shown in FIG. 5, the electrodes 106a-n are communicatively coupled to the electrode holders 104a-n via a communication link 502 such as, for example, the contact formed between the electrode 106a and the electrode holder 104a disclosed above (e.g., FIG. 3). In the example shown in FIGS. 2A, 2B and 3, the electrode holder 104a includes the retainer ring 310, which engages (e.g., contacts) the ribs 224a-n on the sheath 216 to releasably secure and stabilize the electrode 106a within the electrode holder 104a. The electrode pin 218, the sheath 216 and the spring 322 are electrically conductive. Therefore, signals gathered by the electrode pin 218 are transferred through the sheath 216 and to the retainer ring 310 disposed within the electrode holder 104a. In the example shown in FIG. 3, the electrode holder 104a also includes the wire 326 that transfers signals from retainer ring 310 through the base 200 to an outside surface of the base.

As shown in the block diagram of FIG. 5, the electrode holders 104a-n are communicatively coupled to the processing unit 110 via a communication link formed by, for example, wires 108a-n. In some examples, the wires 108a-n are disposed within the material of a cap 102 (e.g., between a top and bottom layer of material). The wires 108a-n communicatively couple each of the electrode holders 104a-n (and their respective electrode 106a-n) to the processing unit 110 of the headset 100. In other examples, the wires 108a-n in the cap 102 connect to a plug on the cap 102, which allows the cap 102 to be plugged into another outside computer or processing station.

The example system 500 of FIG. 5 also includes a reference electrode 109. The reference electrode 109 is coupled to the processing unit 110 via a wire 111. The reference electrode 109 provides a reference signal to compare against the EEG signals gathered by, for example, the electrodes 106a-n. The reference electrode 109 may be attached to the ear, the nose, the neck, or any other suitable place on the person's body having minimal or no EEG activity. For example, in the illustrated example of FIGS. 1A and 1B, the reference electrode 109 is coupled to the ear of the wearer. In some examples, the system 500 includes more than one reference electrode.

The example processing unit 110 of FIG. 5 includes an analog-to-digital converter 504, a signal conditioner 506, a database 508, an analyzer 510 and a transmitter 512.

The analog-to-digital converter 504 converts the analog signals received at the electrodes 106a-n and the reference electrode 109 to digital signals. In some examples, the analog-to-digital converter 504 is located in the processing unit 110 in the housing of the headset. In other examples, the analog-to-digital converter 504 comprises multiple A-D converters located to service individual electrodes or sets of the electrodes to convert the signals as close to the source as possible, which may further reduce interference. In some examples, the A-D converters are disposed within housings of electrode holders 104a-n.

The signal conditioner 506 of the illustrated example prepares the gathered signals so that the data is in a more usable form. For example, the signal conditioner 506 may include an amplifier to amplify the signal to a more detectable level. In addition, the signal conditioner 506 may include a filter to remove noise from the signal. The filter may also be used as a bandpass filter to pass one or more frequency bands and/or manipulate select bands depending on the desired processing and/or analysis. In some examples, each of the electrodes 106a-n and/or the reference electrode 109 may include a signal conditioner at or near the electrode 106a-n or the reference electrode 109. The example signal conditioner 506 may include hardware and/or software to execute a signal conditioning method. In some examples, the signal conditioner includes a detrending unit to compensate for electrode polarization, in which there is slow movement of the voltage signal unrelated to brain wave activity due to polarization of the electrodes. The example processing unit 110 of FIG. 5 also provides signal processing that may include hardware and/or software to execute Fast Fourier Transform (FFT) calculations, coherence measurements and/or custom adaptive filtering.

The analyzer 510 of the illustrated example analyzes the data gathered from the electrodes 106a-n and the reference electrode 109 and processed by the analog-to-digital converter 504 and the signal conditioner 506 in accordance with one or more analysis protocols depending on the desired study. For example, in some studies, the analyzer 510 process the data to determine one or more of a subject's mental state, physiological state, attention, resonance or memory, emotional engagement and/or other suitable characteristics of the subject. Descriptions of example processing operations and techniques are disclosed in U.S. patent application Ser. No. 13/728,900, entitled "SYSTEMS AND METHODS TO GATHER AND ANALYZE ELECTROENCEPHALOGRAPHIC DATA," and filed Dec. 27, 2012, and U.S. patent application Ser. No. 12/056,190 (now U.S. Pat. No. 8,484,081), entitled "ANALYSIS OF MARKETING AND ENTERTAINMENT EFFECTIVENESS USING CENTRAL NERVOUS SYSTEM, AUTONOMIC NERVOUS SYSTEM, AND EFFECTOR DATA," and filed Mar. 26, 2008, both of which are incorporated herein by reference in their entireties.

The transmitter 512 of the illustrated example communicates the data at any stage of processing and/or the results of the analysis from the analyzer 510 to an output 514. The output 514 may be implemented by a handheld device, an alarm, a display screen on the headset, a remote server, a remote computer and/or any other suitable output. In some examples, the output is a display screen and may be used to indicate when an electrode 106a-n is in an electrode holder 104a-n and when the electrode 106a-n is receiving signals. Also, in some examples, the output 514 may be used to indicate that an electrode is 106a-n is not gathering a sufficiently strong signal, according to the signal analysis preformed by the processing unit 110. In such examples, the output 514 may indicate that the electrode 106a-n is to be inserted further into the respective electrode holder 104a-n to improve signal quality.

Data transmission may be implemented by Bluetooth transmission, wi-fi transmission, ZiGBee transmission and/or encryption before transmission. In the illustrated example, the database 508 stores gathered data. The streams can be buffered for streaming or stored on-board (i.e., at the headset) for periodic or aperiodic uploads during, for example, low-activity periods.

The components 504-512 of the processing unit 110 are communicatively coupled to other components of the example system 500 via communication links 516. The communication links 516 may be any type of wired connection (e.g., a databus, a USB connection, etc.) or a wireless communication mechanism (e.g., radio frequency, infrared, etc.) using any past, present or future communication protocol (e.g., Bluetooth, USB 2.0, USB 3.0, etc.). Also, the components of the example system 500 may be integrated in one device or distributed over two or more devices.

While an example manner of implementing the system 500 is illustrated in FIG. 5, one or more of the elements, processes and/or devices illustrated in FIG. 5 may be combined, divided, re-arranged, omitted, eliminated and/or implemented in any other way. Further, the example processing unit 110, the example signal conditioner 506, the example A/D converter 504, the example database 508, the example transmitter 512, the example analyzer 510, the example output 514 and/or, more generally, the example system 500 of FIG. 5 may be implemented by hardware, software, firmware and/or any combination of hardware, software and/or firmware. Thus, for example, any of the example processing unit 110, the example signal conditioner 506, the example A/D converter 504, the example database 508, the example transmitter 512, the example analyzer 510, the example output 514 and/or, more generally, the example system 500 of FIG. 5 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example processing unit 110, the example signal conditioner 506, the example A/D converter 504, the example database 508, the example transmitter 512, the example analyzer 510 or the example output 514 is/are hereby expressly defined to include a tangible computer readable storage device or storage disk such as a memory, a digital versatile disk (DVD), a compact disk (CD), a Blu-ray disk, etc. storing the software and/or firmware. Further still, the example system 500 of FIG. 5 may include one or more elements, processes and/or devices in addition to, or instead of, those illustrated in FIG. 5, and/or may include more than one of any or all of the illustrated elements, processes and devices.

Figure 6:
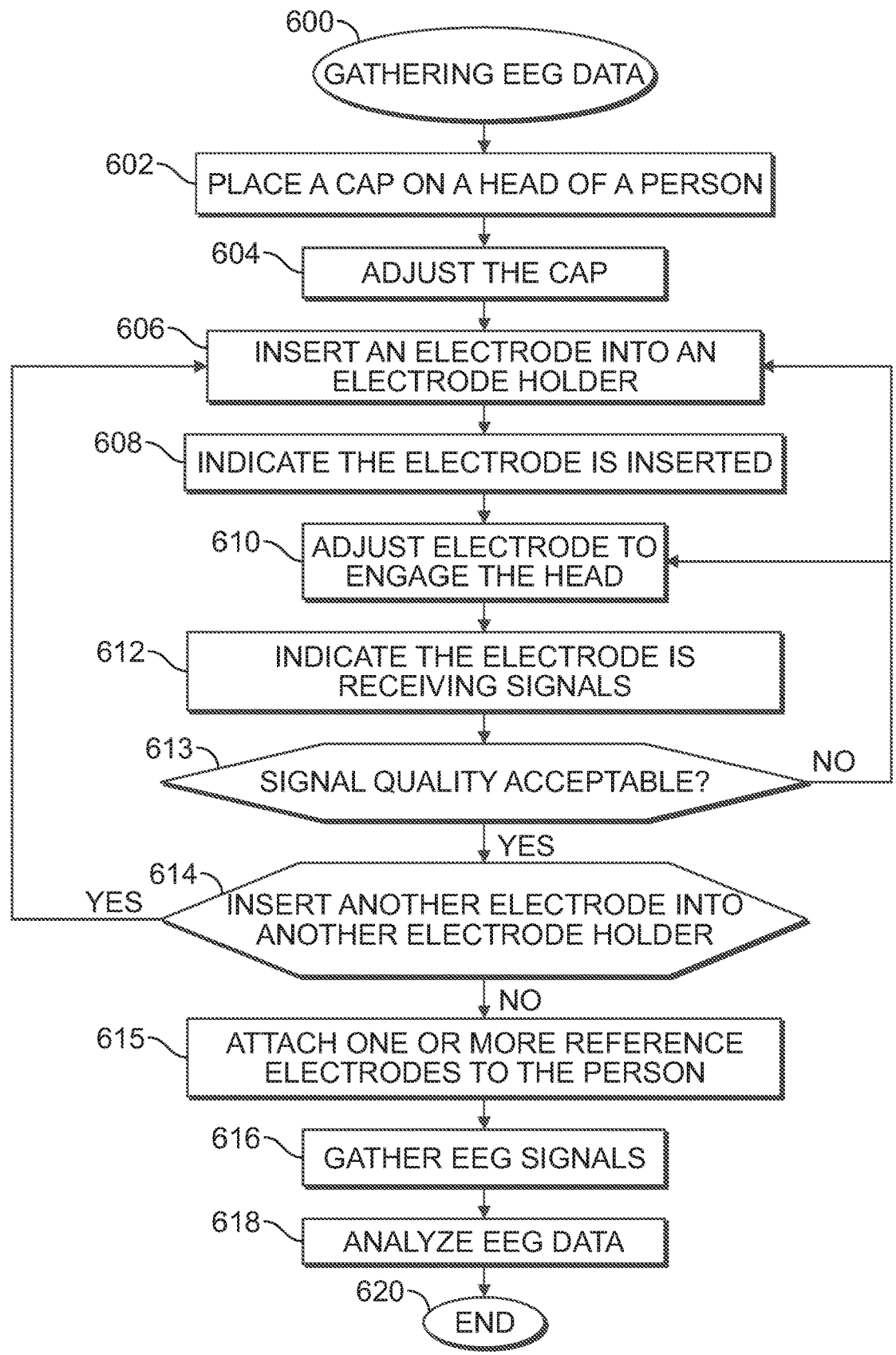
FIG. 6 is a flowchart representing example instructions, at least some of which are machine readable, for implementing the example headset of FIGS. 1A and 1B.
Figure 7:
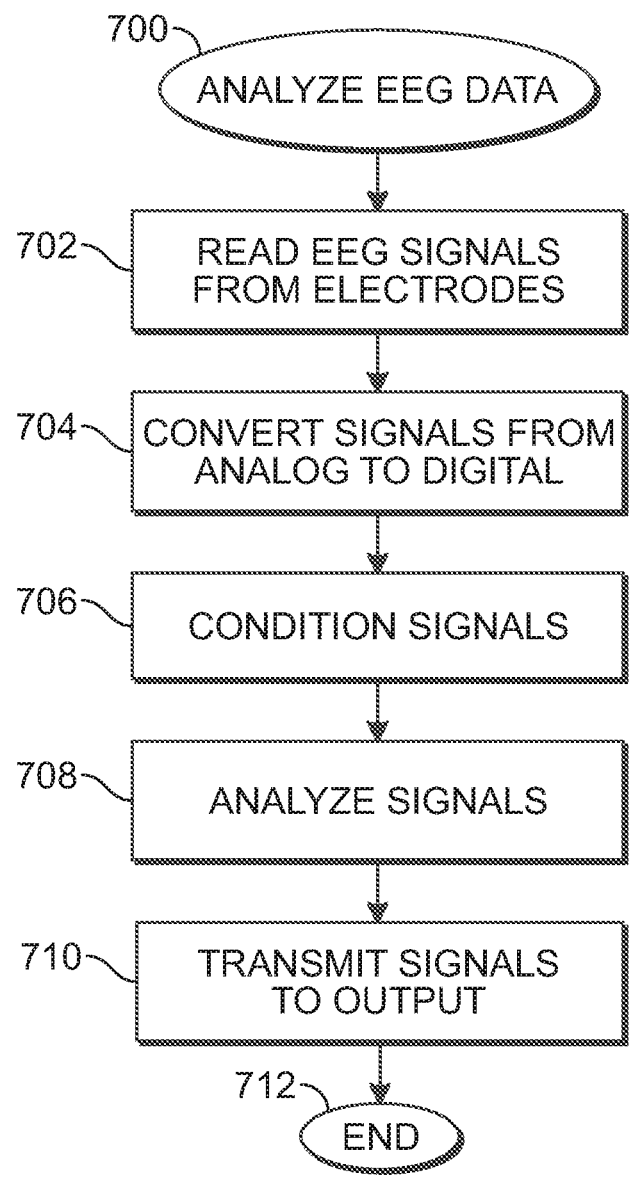
FIG. 7 is a flowchart representative of example machine readable instructions for analyzing EEG data gathered with the example headset of FIGS. 1A and 1B.

Flowchart representations of example instructions, at least some of which are machine readable, for implementing the headset 100 and/or system 500 of FIGS. 1A-5 are shown in FIGS. 6 and 7. In this example, the machine readable instructions comprise a program for execution by a processor such as the processor 812 shown in the example processing platform 800 discussed below in connection with FIG. 8. The program may be embodied in software stored on a tangible computer readable medium such as a CD-ROM, a floppy disk, a hard drive, a digital versatile disk (DVD), or a memory associated with the processor 812, but the entire program and/or parts thereof could alternatively be executed by a device other than the processor 812 and/or embodied in firmware or dedicated hardware. Further, although the example program is described with reference to the flowcharts illustrated in FIGS. 6 and 7, many other methods of implementing the example headset 100 and/or example system 500 may alternatively be used. For example, the order of execution of the blocks may be changed, and/or some of the blocks described may be changed, eliminated, or combined.

As mentioned above, the example process of FIG. 7 and at least a portion of the example process of FIG. 6 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process of FIG. 7 and at least a portion of the example process of FIG. 6 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 6 is a flowchart illustrating an example process of gathering EEG data (block 600) that may be implemented, for example, with the headset 100 disclosed herein. The example process begins by placing a cap (e.g., a base) on a head of a person (block 602) such as for, example, the cap 102 shown in FIGS. 1A and 1B. The example cap 102, as described above, is placed (e.g., stretched over) on the head of a person. The example cap 102 includes the plurality of electrode holders 104a-n that are operatively coupled to the cap 102. The electrode holders 104a-n are disposed on the cap 102 in specific areas for optimum reading.

The example process 600 includes adjusting the cap on the head of the person (block 604). The cap may include one or more buckles and/or straps to secure the cap to the head of the person. In the example headset 100 disclosed above, the cap 102 includes the chin strap 103, which may be adjusted to situate the cap 102 on the person's head.

The example process 600 includes inserting an electrode into an electrode holder (block 606). In some examples, the electrode holder includes an opening or passage formed therein to receive the electrode. In the example headset 100 disclosed above, the electrode holders 104a-n include openings (e.g., opening 204) to receive the electrodes 104a-n. An example one of the plurality of electrodes 106a may be inserted into the opening of an example one of the plurality of electrode holders 104a. The example electrode 106a may be provided in a plurality of different sizes. A longer electrode may be utilized, for example, with persons have longer and/or thicker hair.

The example process 600 includes indicating the electrode is inserted into the electrode holder (block 608). As mentioned above, the wires of the cap may be operatively coupled to a computer or processing station. In some examples, a graphical user interface or other display indicates when an electrode has been inserted into an electrode holder.

The example process 600 includes adjusting the electrode in the electrode holder (block 610). In some examples, the electrode and the electrode holder include features (e.g., engagement members) that enable the electrode to be moved up or down in the electrode holder and, thus, closer or further from the head of the person wearing the cap. In some examples, the features are to secure the electrode in discrete positions in the electrode holder.

In the example headset 100 disclosed above, the electrode 106a includes the plurality of ribs 224a-n. When the electrode 106a is inserted into the electrode holder 104a, the ribs 224a-n engage the first and second springs 314, 316 of the retainer ring 312. The springs 314, 316 are biased radially inwards and secure the electrode 106a in discrete positions in the electrode holder 104a. The electrode 106a can be moved up or down, by supplying a force to the electrode 106a that overcomes the force from the springs 314, 316, to position the electrode 106a closer to or further from the head of the person. As the electrode 106a engages the head of the person, the cap 102 is stretched upward and away from the head of the person, which creates tension in the cap 102. This tension assists in holding the electrode 106a against the head of the person. Additionally, in some examples, the electrode 106a includes the spring 322 that biases the pin 218 outward from the sheath 216. The spring advantageously reduces some of the pressure of the electrode 106a against the scalp to increase wearability.

The example process 600 includes indicating the electrode is receiving signals (block 612). In some examples, the graphical user interface or display may indicate (e.g., via a green light) once the electrode has made contact with the head of the person and is successfully receiving signals from the brain.

In some examples, the example process 600 determines if the signal quality from an electrode is acceptable (block 613). For example, the example processing unit 110 may condition and analyze the gathered signal to assess signal quality. In analyzing the quality of the signal, the processing unit may perform a comparison of the quality to a threshold quality and determining that the quality is acceptable or unacceptable based on the comparison. If the signal quality is poor, that is, not acceptable, the process 600 continues at block 610 to adjust the electrode or at block 606 to insert a different electrode. If the example process 600 determines that the electrode is gathering a signal of acceptable quality (block 613), the process 600 continues.

The example process 600 includes determining whether another electrode is to be inserted into another electrode holder (block 614). In some examples, the headset includes a plurality of electrode holders. In some examples, electrodes are inserted into all of the electrode holders on the cap. However, in other examples, electrodes are inserted into only a subset or group of electrode holders and the remaining electrode holders are empty. In other examples, only one electrode is used. In the example headset 100 disclosed above, any amount of example electrode holders 104a-n may be operatively coupled to the cap 102, and electrodes may be inserted in one or more of the electrode holders 104a-n.

If it is determined that another electrode is to be inserted into another electrode holder for gathering signals, the process 600 includes inserting another electrode into another electrode holder (block 606).

The example process 600 includes attaching one or more reference electrodes to the person (block 615). In some examples, an electrode is utilized to provide reference signal to compare against the other EEG signals. In the example headset 100 disclosed above, the reference electrode 109 is attached to the ear of the wearer and is communicatively coupled to the processing unit 110 via the wire 111.

After inserting one or more electrodes into one or more electrode holders, the example process 600 includes gathering EEG signals from the electrodes of the headset (block 616). In the example headset 100 disclosed above, the cap 102 includes wires 108a-n that are communicatively coupled to the respective electrode holders 104a-n. The electrodes 106a-n receive signals from the head of the person and the signals are transmitted through the respective electrode holders 106a-n to the wires 108a-n. The wires 108a-n (and the wire 111 of the reference electrode 109) are coupled to, for example, the processing unit 110. In other examples, the wires 108a-n, 111 are operatively coupled to a plug, which may be plugged into another line and connected to an outside computer or processing station. In still other examples, the wires 108a-n, 111 are operatively coupled to an amplifier/transmitter, which amplifies the signals and then transmits them, wirelessly, to an outside computer or processing station.

The example process 600 includes analyzing the EEG signals (block 618). An example process of analyzing EEG data is discussed in FIG. 7. Once the analyzing is complete, the example method 600 ends (block 620).

FIG. 7 is a flowchart representative of example instructions which may be executed to analyze EEG data (block 700) collected from the example headset 100. The example headset 100 has a plurality of electrodes that contact the scalp of a subject to receive electrical signals from the subject's brain. The example process of analyzing EEG data (block 700) includes reading the EEG signals from the electrodes (block 702). In the illustrated example, the signals are converted from an analog signal to a digital signal (block 704). In some examples, the analog-to-digital conversion takes place in a processing unit, such as, for example, the processing unit 110 of the example system 500. In other examples, the analog-to-digital conversion takes place adjacent the electrodes within the headset to convert the signal as close to the source as possible.

In the illustrated example, the signals are conditioned (block 706) to improve the usefulness of the signals and the accessibility of the data contained therein. For example, as disclosed above, the conditioning may include amplifying the signals and/or filtering the signals (e.g., with a bandpass filter).

The signals are analyzed (block 708) to, for example, determine a mental state of the subject, a health condition, an engagement with media as an audience member or effectiveness of the media, and/or an input desire for an electrical device. For example, the EEG data may be analyzed to evaluate brain activity in particular frequency bands of the EEG data and/or in particular regions of the brain. Assessments and/or calculations of the relationship(s) and correlation(s) of the frequency bands and regions of activity of the EEG data may be used to determine an emotional or mental state of a person including, for example, attention, emotional engagement, memory or resonance, etc. A description of other processing operations and techniques is disclosed in U.S. patent application Ser. No. 13/829,849 titled "METHODS AND APPARATUS TO GATHER AND ANALYZE ELECTROENCEPHALOGRAPHIC DATA," filed Mar. 14, 2013, which is incorporated herein by reference in its entirety.

In the illustrated example, the signals (e.g., the results of the analysis) are transmitted to an output (block 710), such as, for example, the output 514 of the example system 500. Example modes of output include, for example, sounding an alarm, displaying a message and/or other alert on a screen, issuing a report to a local and/or remote computer and/or any other suitable output. In addition, the output may include the wired or wireless communications detailed herein. In some examples, the output includes data reflected of a person paying attention, the person not paying attention, the person in a state of semi-involvement with a media program, or other mental state of the person, and the identity of the program are transmitted to, for example a remote data facility. Raw data, processed data, a history log or an indicator of audience measurement also may be transmitted to the remote data for collection. The remote data facility may be, for example, a marketing company, a broadcast company, an entertainment studio, a television network and/or any other organization that might benefit from or otherwise desire to know when people are and/or are not focused on broadcast programs and what those programs are. This example allows broadcasting companies and/or marketing personnel to analyze which programs people are watching, when they are watching the programs and/or when they are focused during the broadcast. After the output (block 710), the example process 700 ends (block 712).

Figure 8:
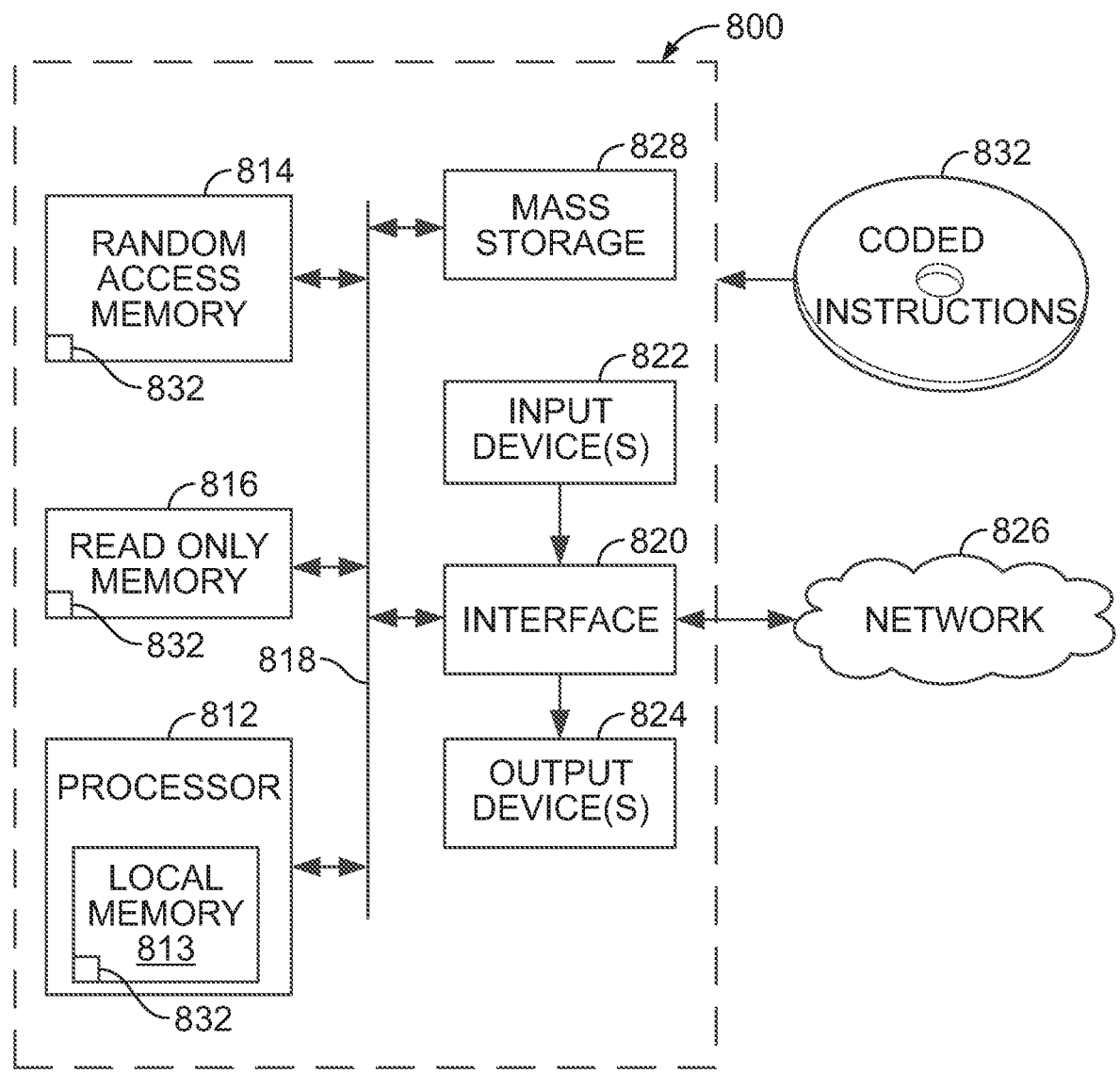
FIG. 8 illustrates an example processor platform that may execute one or more of the instructions of FIGS. 6 and/or 7 to implement the example headset of FIGS. 1A and 1B.

FIG. 8 is a block diagram of an example processing platform 800 capable of executing the one or more of the instructions of FIGS. 6 and 7 to implement one or more portions of the apparatus and/or systems of FIGS. 1A, 1B, 2A, 2B, 3, 4 and 5. The processing platform 800 can be, for example, a processor in a headset, a server, a personal computer, a mobile device (e.g., a cell phone, a smart phone, a tablet such as an iPad™), a personal digital assistant (PDA), an Internet appliance and/or any other type of computing device.

The processor platform 800 of the illustrated example includes a processor 812. The processor 812 of the illustrated example is hardware. For example, the processor 812 can be implemented by one or more integrated circuits, logic circuits, microprocessors or controllers from any desired family or manufacturer.

The processor 812 of the illustrated example includes a local memory 813 (e.g., a cache). The processor 812 of the illustrated example is in communication with a main memory including a volatile memory 814 and a non-volatile memory 816 via a bus 818. The volatile memory 814 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 816 may be implemented by flash memory and/or any other desired type of memory device. Access to the main memory 814, 816 is controlled by a memory controller.

The processor platform 800 of the illustrated example also includes an interface circuit 820. The interface circuit 820 may be implemented by any type of interface standard, such as an Ethernet interface, a universal serial bus (USB), and/or a PCI express interface.

In the illustrated example, one or more input devices 822 are connected to the interface circuit 820. The input device(s) 822 permit(s) a person to enter data and commands into the processor 812. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 824 are also connected to the interface circuit 820 of the illustrated example. The output devices 824 can be implemented, for example, by display devices (e.g., a light emitting diode (LED), an organic light emitting diode (OLED), a liquid crystal display, a cathode ray tube display (CRT), a touchscreen, a tactile output device and or a light emitting diode (LED). The interface circuit 820 of the illustrated example, thus, typically includes a graphics driver card, a graphics driver chip or a graphics driver processor.

The interface circuit 820 of the illustrated example also includes a communication device such as a transmitter, a receiver, a transceiver, a modem and/or network interface card to facilitate exchange of data with external machines (e.g., computing devices of any kind) via a network 826 (e.g., an Ethernet connection, a digital subscriber line (DSL), a telephone line, coaxial cable, a cellular telephone system, etc.).

The processor platform 800 of the illustrated example also includes one or more mass storage devices 828 for storing software and/or data. Examples of such mass storage devices 828 include floppy disk drives, hard drive disks, compact disk drives, Blu-ray disk drives, RAID systems, and digital versatile disk (DVD) drives.

The coded instructions 832 of FIGS. 6 and 7 may be stored in the mass storage device 828, in the volatile memory 814, in the non-volatile memory 816, and/or on a removable tangible computer readable storage medium such as a CD or DVD.

Although certain example apparatus have been described herein, the scope of coverage of this patent is not limited thereto. On the contrary, this patent covers all methods, apparatus, and articles of manufacture fairly falling within the scope of the appended claims either literally or under the doctrine of equivalents.

What is claimed is:

1. A headset comprising:
   a cap to be worn on a head of a person, the cap including a first opening; and
   an electrode holder including:
      a base in the first opening of the cap, the base including a second opening aligned with the first opening; and
      a grip cantilevered from the base the grip extending upward from the cap and away from a central axis of the second opening such that a gap is defined between the grip and the cap, the gap sized to receive a finger of a user, the gap maintained while an electrode is inserted through the second opening toward the head of the person.

2. The headset of claim 1, wherein the grip is a first grip and the gap is a first gap, the electrode holder further including a second grip extending upward from the cap and away from the central axis of the second opening such that a second gap is defined between the second grip and the cap.

3. The headset of claim 2, wherein the second grip extends away from the central axis of the second opening in a direction opposite of the first grip.

4. The headset of claim 2, wherein the finger is a first finger, wherein the first gap is positioned to receive the first finger of the user, and the second gap is positioned to receive a second finger of the user.

5. The headset of claim 1, further including the electrode.

6. The headset of claim 5, wherein the electrode includes a housing and a pin extending from a first end of the housing.

7. The headset of claim 6, wherein the housing includes a handle having a plurality of grips or ribs.

8. The headset of claim 7, wherein the handle is operable to change a position of the electrode relative to the second opening.

9. The headset of claim 7, wherein the handle is an insulator.

10. The headset of claim 5, wherein the electrode holder is a first electrode holder, further including a second electrode holder having a third opening defined through the cap, the electrode insertable into the third opening.

11. The headset of claim 5, wherein the electrode is removable from the cap.

12. The headset of claim 5, wherein the electrode is a first electrode, further including a second electrode interchangeable with the first electrode and insertable into the second opening.

13. The headset of claim 1, wherein the base has a groove in an outer surface of the base, and the cap extends into the groove.

14. An apparatus comprising:
   a cap be worn on a head of a person, the cap including a first opening;
   an electrode holder including:
      a base coupled to the cap at the first opening, the base including a second opening aligned with the first opening;
      a first grip cantilevered from the base, the first grip extending upward from the base and away from a central axis of the second opening; and
      a second grip cantilevered from the base, the second grip extending upward from the base and away from the central axis of the second opening; and
   an electrode insertable into the second opening of the base, the first grip and the second grip to provide leverage when changing a position of the electrode relative to the second opening.

15. The apparatus of claim 14, wherein the second grip extends away from the central axis of the second opening in a direction opposite of the first grip.

16. The apparatus of claim 14, wherein the electrode includes a housing, a pin extending from a first end of the housing, and a handle coupled to a second end of the housing.

17. A method comprising:
   placing a cap of a headset on a head of a person, the cap including a first opening, the headset including an electrode holder, the electrode holder including:
      a base in the first opening of the cap, the base including a second opening aligned with the first opening;
      a grip cantilevered from the base the grip extending upward from the cap and away from a central axis of the second opening such that a gap is defined between the grip and the cap, the gap sized to receive a finger of a user; and
      a retainer coupled within the second opening;
   inserting an electrode into the second opening while the cap is disposed on the head of the person, the gap maintained while the electrode is inserted into the second opening and toward the head of the person, the electrode including an elongated sheath having a plurality of ribs to engage the retainer; and
   adjusting a depth of the electrode within the second opening by removably securing the electrode in one of a plurality of discrete positions having different depths of insertion relative to the second opening defined by an interface between the plurality of ribs and the retainer, the grip to provide leverage when changing the depth of the electrode.

18. The method of claim 17, further including indicating, via a display screen, when the electrode is inserted in the second opening and engaged with the retainer.

19. The method of claim 18, further including indicating, via the display screen, when the electrode is in contact with the head of the person.

20. The method of claim 17, further including:
analyzing a quality of a signal gathered by the electrode;
performing a comparison of the quality to a threshold quality;
determining that the quality is acceptable or unacceptable based on the comparison; and
indicating, via a light, whether the quality is unacceptable.

* * * * *